(12) United States Patent
Morita et al.

(10) Patent No.: US 7,060,108 B2
(45) Date of Patent: Jun. 13, 2006

(54) HAIR DYEING PROCESS

(75) Inventors: Kenichi Morita, Tokyo (JP); Akihiro Sato, Tokyo (JP)

(73) Assignee: Kao Corporation, Tokyo (JP)

( * ) Notice: Subject to any disclaimer, the term of this patent is extended or adjusted under 35 U.S.C. 154(b) by 279 days.

(21) Appl. No.: 10/321,386

(22) Filed: Dec. 18, 2002

(65) Prior Publication Data

US 2003/0150067 A1    Aug. 14, 2003

(30) Foreign Application Priority Data

Dec. 26, 2001  (JP)  ............... 2001-394410

(51) Int. Cl.
*A61K 7/13*    (2006.01)
(52) U.S. Cl. .............. 8/405; 8/406; 8/408; 8/435; 8/618; 8/620; 8/623; 132/202; 132/208
(58) Field of Classification Search .............. 8/405, 8/406, 408, 622, 623, 624, 628, 401, 435, 8/618, 620; 131/202, 208
See application file for complete search history.

(56) References Cited

U.S. PATENT DOCUMENTS

| 5,368,610 A | 11/1994 | Chan et al. ............. 8/406 |
| 5,520,707 A | 5/1996 | Lim et al. .............. 8/426 |
| 6,648,925 B1 * | 11/2003 | Mayer et al. ........... 8/405 |

FOREIGN PATENT DOCUMENTS

| EP | 0 046 543 | 3/1982 |
| EP | 0 621 029 | 10/1994 |
| JP | 53-72836 | 6/1978 |
| JP | 62-126114 | 6/1987 |
| JP | 2-53715 | 2/1990 |
| JP | 5-507106 | 10/1993 |
| JP | 7-82120 | 3/1995 |
| JP | 7-82121 | 3/1995 |
| WO | WO 98/51269 | 11/1998 |
| WO | WO 99/36034 | 7/1999 |
| WO | WO 00/38630 | 7/2000 |

OTHER PUBLICATIONS

Chemical Abstracts, XP-002268533, JP 45-024478, Aug. 14, 1970.*
Chemical Abstracts, XP-002268533, XP-002268687, JP 45-024478, Aug. 14, 1970.
Chemical Abstracts, XP-002268534, JP 48-023910, Jul. 17, 1973.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Hair can be dyed by applying an oxidizing-agent-free, air-oxidative, one-pack hair dye composition to the hair without mixing the hair dye composition with an oxidizing agent and, after the hair is left over for 5 minutes to 1 hour, rinsing off the hair dye composition with water. The hair dye composition comprises:
  (a) a water soluble salt of a transition metal: 0.001 to 10 wt. % in terms of an anhydride based on the whole composition,
  (b) a chelating agent capable of coordinating on said transition metal: 0.001 to 10 wt. % based the whole composition, and
  (c) a color-developing substance: 0.001 to 10 wt. % based on the whole composition.

According to the present invention, hair can be dyed by a convenient procedure without damage. The present invention is also excellent in dyeing properties and color variations.

10 Claims, No Drawings

HAIR DYEING PROCESS

TECHNICAL FIELD

This invention relates to a hair dyeing process, which makes use of an air-oxidative one-pack hair dye composition and is superb in dyeing convenience, gives no damage to hair, and is excellent in dyeing properties and color variations.

BACKGROUND ART

In general, an oxidative hair color is composed of a first pack, which contains an oxidative dye precursor (color-developing substance) as a dye ingredient, a coupling substance and the like, and a second pack containing an oxidizing agent such as hydrogen peroxide, and these first and second packs are mixed together immediately before applying the oxidative hair color to the hair. As an alkaline condition is preferred in an oxidation step of the dye precursor from the viewpoint of color developing property, the first pack is generally formulated to be alkaline such that alkalinity is also maintained after the mixing. In a hair dyeing treatment, the hair is, therefore, exposed to an alkali and the oxidizing agent such as hydrogen peroxide so that the hair is unavoidably damaged.

With a view to overcoming the above-described problem, proposals have been made including: hair coloring techniques each of which makes use of a catalyst to allow a sufficient dyeing reaction to proceed even with a small amount of an oxidizing agent or with a weak oxidizing agent (U.S. Pat. No. 5,368,610); and hair coloring techniques each of which permits induction of an oxidation reaction with oxygen in the air without using any oxidizing agent. These air-oxidative hair coloring techniques include inter alia one making use of an oxidase such as laccase (WO 99/36034), one employing 2,4-diaminophenol which is an oxidative dye of low oxidation potential (JP-A-07082120 or JP-A-02053715), and one making use of an indoline which is a melanine precursor (JP-A-05507106).

The technique disclosed in U.S. Pat. No. 5,368,610, however, uses an oxidizing agent as a matter of fact and hence, cannot fully avoid a damage to hair. Concerning its hair dye composition, there is no choice other than formulating the composition into a two-pack, mixing at-need form. Further, the dyeing procedure is irksome. The process making use of an oxidase, on the other hand, is accompanied by a problem that, as the enzyme has a high molecular weight, its dye-oxidizing action can be hardly allowed to extend into hair fibers and no sufficient dyeing power is available and also by a problem that limitations are imposed on a surfactant, a solvent and the like, which are to be used in combination upon formulation, to avoid losing the activity of the enzyme. When 2,4-diaminophenol, a dye of low oxidation potential, is used, there is a concern about the safety of this compound. Use of an indoline, on the other hand, involves a limitation that color variations are limited because usable dyes are limited by the indoline itself.

DISCLOSURE OF THE INVENTION

An object of the present invention is to solve these conventional problems and to provide a hair dyeing process, which is superb in dyeing convenience, gives no damage to hair, and is excellent in dyeing properties and color variations. Specifically, the present invention has as an object the provision of a hair dyeing process relying upon a one-pack hair dye composition which uses a conventional oxidative dye and does not contain any oxidizing agent.

The present inventors found that addition of a water-soluble transition metal salt and a chelating agent in combination to an oxidative dye can oxidize the oxidative dye by the action of a complex formed from the metal salt and a chelating agent. Base on the above finding, it has become possible to conduct the dyeing of hair with an oxidative dye without using an oxidizing agent such as hydrogen peroxide or a chlorite and also without needing to establish an alkaline state. As no oxidizing agent is used, filling of the oxidative dye together with other ingredients in a sealed container can maintain the oxidative dye in its preserved state, thereby making it possible to formulate the oxidative dye and other ingredients into a simple one-pack preparation. Owing to these characteristic features, the hair dyeing process according to the present invention can avoid damage to hair, is simple and convenient in procedure, and is also excellent in dyeing properties and color variations owing to the usability of various oxidative dyes.

Described specifically, the present invention provides a hair dyeing process comprising applying an oxidizing-agent-free, air-oxidative, one-pack hair dye composition, which comprises the following ingredients (a) to (c):

(a) a water soluble salt of a transition metal: 0.001 to 10 wt. % in terms of an anhydride form based on the whole composition, (b) a chelating agent capable of coordinating on the transition metal: 0.001 to 10 wt. % based the whole composition, and (c) a color-developing substance: 0.001 to 10 wt. % based on the whole composition, to hair without mixing the hair dye composition with an oxidizing agent and, after the hair is left over for 5 minutes to 1 hour, rinsing off the hair dye composition with water.

BEST MODES FOR CARRYING OUT THE INVENTION

Examples of the water-soluble salt of the transition metal employed as the ingredient (a) in the present invention can include the hydrochlorides, sulfates, nitrates, carbonates, hydrogencarbonates, phosphates, organic acid salts and the like of metals such as iron, copper, zinc, cobalt, nickel, manganese and silver. Among these, particularly referred from the standpoint of safety are iron salts, for example, ferrous sulfate, ferric sulfate, ferrous chloride and ferric chloride.

Two or more water-soluble transition metal salts can be used in combination as the ingredient (a). The content of the ingredient (a) can be set at 0.001 wt. % or higher in terms of an anhydride form based on the whole composition from the standpoint of dyeing property improving effects and at 10 wt. % or lower from the standpoint of avoidance of a remaining metal smell (especially in the case of an iron salt) and also prevention of reductions in touch and sleekness. Preferably, the content of the ingredient (a) may range from 0.01 to 5 wt. % in terms of an anhydride form based on the whole composition, with 0.1 to 3 wt. % being particularly preferred. Incidentally, the term "the whole composition" as used herein should not include a propellant when the composition is formulated into an aerosol.

The chelating agents (b) capable of coordinating on the transition metal ions derived from the ingredient (a) may be those commonly employed in cosmetics. Illustrative are ethylenediaminetetraacetic acid, hydroxyethylethylenediaminetriacetic acid, diethylenetriaminepentaacetic acid, nitrilotriacetic acid, triethylenetetraminehexaacetic acid, ethylenediaminedisuccinic acid, cyclam, phosphonic acids, tripolyphosphoric acid, ascorbic acid, citric acid, maleic acid, and salts thereof (except for transition metal salts). Among these, those equipped with a function to incorporate surrounding oxygen into a complex upon formation of the complex by chelating metal ions derived from the ingredient (a) are preferred from the standpoint of dyeing properties. From this viewpoint, preferred are ethylenediaminetetraacetic acid, hydroxyethylethylenediaminetriacetic acid, nitrilotriacetic acid, cyclam, ethylenediaminedisuccinic acid and salts thereof (except for transition metal salts).

Two or more chelating agents can be used in combination as the ingredient (b). The content of the ingredient (b) is set at 0.001 to 10 wt. % based on the whole composition, with 0.01 to 5 wt. % being preferred and 0.1 to 3 wt. % being particularly preferred. From a relationship between the coordination number of the metal and the number of coordination positions which the chelating agent has, the contents of the ingredients (a) and (b) can be set such that [the number of moles of the transition metal in the component (a)]/[the number of moles of the component (b)] ranges preferably from 1/10 to 10/1, more preferably from 1/5 to 5/1, especially from 1/3 to 3/1.

Examples of the color-developing substance as the ingredient (c) can include p-phenylenediamines having one or more NH$_2$— groups, NHR— groups or NR$_2$— groups wherein R represents an alkyl group having 1 to 4 carbon atoms or a hydroxyl group, such as p-phenylenediamine, p-toluylenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, 2-(2'-hydroxyethylamino)-5-aminotoluene, 2-(2-hydroxyethyl)-p-phenylenediamine, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, and N-2-methoxyethyl-p-phenylenediamine; 2,5-diaminopyridine derivatives; p-aminophenols such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol, and 5-aminosalicylic acid; o-aminophenols; o-phenylenediamines; and tetraaminopyrimidine, 5,6-dihydroxyindole, 5,6-diacetoxyindole, 5,6-dihydroxyindoline, and 5,6-dihydroxyindoline-2-carboxylic acid. Among these, p-phenylenediamine, p-toluenediamine, 2-(2-hydroxyethyl)-p-phenylenediamine, p-aminophenol and tetraaminopyrimidine are preferred from the standpoint of dyeing properties.

Two or more color-developing agents can be used in combination. The content of the ingredient (c) may range from 0.001 to 10 wt. %, preferably from 0.01 to 5 wt. %, especially from 0.1 to 4 wt. %, all based on the whole composition.

Further, a coupling substance can also be used as an ingredient (d) in combination as needed. Selection of a desired coupling substance makes it possible to dye hair in a preferred color. Examples of the coupling substance can include α-naphthol, o-cresol, m-cresol, 2,6-dimethylphenol, 2,5-dimethylphenol, 3,4-dimethylphenol, 3,5-dimethylphenol, benzcatechin, pyrogallol, propyl gallate, 1,5-idihydroxynaphthalene, 1,7-dihydroxynaphthalene, 5-amino-2-methylphenol, 5-(2'-hydroxyethylamino)-4-methoxyphenol, hydroquinone, 2,4-diaminoanisole, m-toluenediamine, 4-aminophenol, resorcine, resorcine monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxy-2-quinolone, m-aminophenol, 4-chlororesorcine, 2-methylresorcine, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, and 4,6-diamino-2-hydroxypyrimidine. Among these, those capable of reacting the precursor to form a dimer are preferred from the standpoint of penetrating property of the dye and dyeing properties, including 2,4-diaminophenoxyethanol, 5-amino-2-methylphenol and the like.

Two or more coupling substances can be used in combination. The content of the ingredient (d) may range preferably from 0.001 to 10 wt. %, more preferably from 0.01 to 5 wt. %, especially from 0.1 to 4 wt. %, all based on the whole composition.

The present invention features the use of a hair dye composition free of an oxidizing agent such as hydrogen peroxide despite the use of an oxidative dye precursor which generally requires such an oxidizing agent for the development of a color. Relying solely upon its contact with oxygen in the air during use, the dye precursor is subjected to oxidative polymerization such that the color is developed to dye hair. The exclusion of an oxidizing agent has an advantageous effect that damages to the hair and scalp can be suppressed. It is effective to increase the area of contact with the air to promote an oxidative reaction. It is, therefore, preferred to form the hair dye composition into a foam or thin films. As a means for forming the hair dye composition into a foam, its formulation into an aerosol can be mentioned. In view of the characteristic feature of the present invention that the hair dye composition is of the air oxidation type, it is preferred for the foam to entrap air therein. Described specifically, it is particularly preferred that concurrently with ejection of the hair dye composition, the hair dye composition draws the surrounding air thereinto and turns into a foam. In this case, the density of the foam so ejected may range preferably from 0.02 to 1 g/mL, especially from 0.1 to 0.9 g/mL.

Examples of a propellant which is used upon formulation of the hair dye composition into an aerosol can include liquefied petroleum gas (LPG), saturated lower hydrocarbons, dimethyl ether, nitrogen gas, carbon dioxide gas, and argon gas. Among these, LPG, dimethyl ether, nitrogen gas and carbon dioxide gas are preferred. The hair die composition can be filled preferably in a pressure-resistant, oxygen-tight container under anaerobic conditions. Illustrative of the container are aerosol containers and PET container. It is also preferred to form the container into a double-wall container or the like.

To lower the surface tension of the hair dye composition so that its formation into a foam upon ejection or its formation into a foam or a thin film upon coating can be facilitated, it is preferred to add as an ingredient (e) a surfactant selected from various nonionic, anionic, cationic and amphoteric surfactants. It is preferred to select a surfactant of a type that is most suitable from its relationship with the other ingredients. It is preferred to select a surfactant as desired depending upon the situation. When a cationic polymer is added as a touch improver, it is preferred to choose one of surfactants other than anionic surfactants from the viewpoint of prevention of formation of a complex. When no cationic polymer is added as a touch improver, it is preferred to select a cationic surfactant or an amphoteric surfactant from the viewpoint of improvements in touch or an anionic surfactant from the viewpoint of stability of a foam.

Examples of the nonionic surfactants can include polyoxyethylene alkyl ethers such as polyoxyethylene oleyl ether and polyoxyethylene stearyl ether; polyoxyethylene alkyl phenyl ethers such as polyoxyethylene nonyl phenyl ether and polyoxyethylene octyl phenyl ether; and alkyl polyglucosides, polyoxyethylene sorbitan fatty acid esters, fatty acid alkylolamides, and polyoxyethylene sec-tetradecyl ether. Particularly preferred are polyoxyethylene(9) tridecyl ether and alkylpolyglucosides.

Examples of the anionic surfactant can include alkylbenzene sulfonates, alkyl sulfates, alkyl ether sulfonates, polyoxyethylene alkyl ether sulfates, olefinsulfonates, alkanesulfonates, saturated or unsaturated fatty acid salts, alkyl ether carbonates, α-sulfo fatty acid salts, N-acyl amino acid surfactant, phosphate mono- or diester surfactants, and sulfosuccinate esters. Particularly preferred are alkyl ether sulfates and polyoxyethylene alkyl ether sulfates.

Examples of the cationic surfactant can include imidazoline quaternary ammonium salts, mono(long-chain alkyl) quaternary ammonium salts, and di(long-chain alkyl) quaternary ammonium salts. Particularly preferred are stearyl trimethyl ammonium and cetyl trimethyl ammonium.

Examples of the amphoteric surfactant can include surfactants of the imidazoline type, carbobetaine type, amidobetaine type, sulfobetaine type, hydroxysulfobetaine type, aminosulfobetaine type and amine oxide type.

The content of the surfactant may range preferably from 0.01 to 10 wt. %, more preferably from 0.1 to 5 wt. %, and especially from 0.5 to 3 wt. %, all based on the whole composition.

To the dye composition, a cationic polymer can be added further as a touch improver. Examples of the cationic polymer can include cationized cellulose derivatives, cationic starch, cationized guar gum derivatives, homopolymer of diallyl quaternary ammonium salt, diallyl quaternary ammonium salt/acrylamide copolymer (e.g.; Polyquaternium-7), quaternized polyvinylpyrrolidone derivatives, polyglycol polyamine condensation products, vinylimidazolium trichloride/vinylpyrrolidone copolymer, hydroxyethylcellulose/dimethyldiallylammonium chloride copolymer, vinylpyrrolidone/quaternized dimethylaminoethyl methacrylate copolymer, polyvinylpyrrolidone/alkyl amino-acrylate copolymers, polyvinylpyrrolidone/alkyl amino-acrylate/vinyl caprolactam copolymers, vinylpyrrolidone/methacrylamidopropyl chlorotrimethylammonium copolymer, alkyl acrylamide/acrylate/alkylaminoalkylacrylamide/polyethylene glycol methacrylate copolymers, adipic acid/dimethylaminohydroxypropyl ethylenetriamine copolymer("Cartaretin", trademark; product of Sandoz Chemicals Corp., U.S.A), and cationic polymers disclosed in JP-A-53139734 or JP-A-60036407. Of these, the cationized cellulose derivatives and the cationized guar gum derivatives are particularly preferred.

Two or more cationic polymer can be used in combination. The content of the cationic polymer may range preferably from 0.001 to 30 wt. %, especially from 0.01 to 10 wt. %, both based on the whole composition.

To prevent dripping upon ejection and to facilitate uniform application to hair, a viscosity increasing agent may preferably be added to the hair dye composition. Examples of the viscosity increasing agents can include cellulose derivatives such as hydroxyethylcellulose, an ether of hydroxyethylcellulose and glycidyltrimethylammonium chloride, methylcellulose and carboxymethylcellulose; natural gums such as xanthan gum and guar gum; polyvinylpyrrolidone, crosslinked polyacrylic acid and its salts, polyacrylic acid and its salts, and polyacrylamide. In general, xanthan gum or the like is preferred for its high salt resistance. When a cationic surfactant or a cationic polymer is used as a touch improver, an anionic high-molecular viscosity increasing agent such as carboxymethylcellulose forms a water-insoluble complex. From the viewpoint of avoiding formation of a complex, use of a nonionic high-molecular viscosity increasing agent such as hydroxyethylcellulose is preferred.

Two or more viscosity increasing agents may be used in combination. The content of the viscosity increasing agent may range preferably from 0.01 to 30 wt. %, especially from 0.1 to 10 wt. %, both based on the whole composition.

To make the color-developed dye molecule penetrate more effectively into hair fibers, the hair dye composition may further contain an organic solvent selected from the following compounds (i) to (iv).

(i) Compounds represented by the following formula (1):

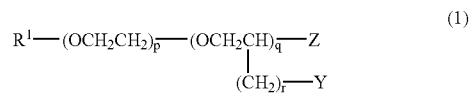

(1)

wherein $R^1$ represents a hydrogen atom, a lower alkyl group or a group represented by the following formula:

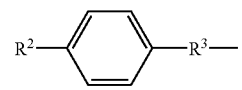

wherein $R^2$ represents a hydrogen atom, a methyl group or a methoxy group, and $R^3$ represents a single bond or a saturated or unsaturated divalent hydrocarbon group having 1 to 3 carbon atoms, Y and Z each independently represents a hydrogen atom or a hydroxy group, and p, q and r each independently denotes an integer of from 0 to 5, with a proviso that Z is not a hydrogen atom when p=q=0 and also that Z is not a hydroxy group when p=q=0 and $R^1$ is a hydrogen atom.

(ii) Compounds represented by the following formula (2):

(2)

wherein $R^4$ represents a linear or branched alkyl group having 1 to 18 carbon atoms.

(iii) Alkylene carbonates having 2 to 5 carbon atoms.

(iv) 5-Membered or 6-membered, cyclic lactones with one or more alkyl, alkenyl, alkoxy and/or acyl groups substituted thereon.

Specific examples of these organic solvents can include ethanol, 1-propanol, 2-propanol, 1-butanol, isobutanol, ethylene glycol, propylene glycol, benzyl alcohol, cinnamyl alcohol, phenethyl alcohol, p-anisyl alcohol, p-methylbenzyl alcohol, phenoxyethanol, 2-benzyloxyethanol, methyl carbitol, ethyl carbitol, propyl carbitol, butyl carbitol, triethylene glycol monoethyl ether, triethylene glycol monobutyl ether, glycerin, N-methylpyrrolidone, N-octylpyrrolidone, N-laurylpyrrolidone, ethylene carbonate, propylene carbonate, γ-butyrolactone, γ-pentanolactone, δ-pentanolactone, γ-hexanolactone, δ-hexanolactone, γ-heptanolactone, δ-heptanolactone, γ-octanoic acid lactone, and α-methyl-γ-butyrolactone. Among these, preferred are benzyl alcohol, phenoxyethanol, 2-benzyloxyethanol, γ-butyrolactone, γ-pentanolactone, and γ-hexanolactone.

Two or more of these organic solvents can be used in combination. The content of the organic solvents may range preferably from 0.1 to 50 wt. %, more preferably from 1 to 30 wt. %, and especially from 5 to 20 wt. %, all based on the whole composition.

In addition to the above-described ingredients, one or more of additional ingredients employed in ordinary hair dye compositions may be added to the dye composition for use in the present invention as needed to extent not impairing the advantageous effects of the present invention. Illustrative of these additional ingredients are higher alcohols, stabilizers, buffering agents, fragrances, touch improvers other than those described above, solubilizers, alcohols other than those described above, alcohols such as polyols, direct dyes such as nitro dyes, oxidative dyes, basic dyes and disperse dyes, oxidation inhibitors such as ascorbic acid and sodium sulfite, and preservatives.

Unlike the oxidative two-pack hair dye composition, the dye composition for use in the present invention is not limited to an alkaline condition but can be formulated with a pH of from 4 to 11. Since the polymerization reaction of the oxidative dye takes place too fast under a high pH condition, the pH range is preferably from 5 to 9, more preferably from 5.5 to 8.5, most preferably from 6 to 8.

The hair dyeing process according to the present invention can be practiced preferably by dispensing an appropriate amount of the air-oxidative, one-pack hair dye composition onto a comb or the like from a container filled with the hair dye composition, applying the hair dye composition to hair and, after the hair is left over for 5 minutes to 1 hour, rinsing off the hair dye composition with water. The amount to be applied is generally at a ratio of about 1:1 relative to the weight of hair, although it can be suitably adjusted depending on the condition of the hair and the dyeing properties. Further, the left-over time after the application can also be adjusted depending upon preference on the basis of the condition of the hair and the dyeing properties.

EXAMPLES

Examples 1–9 and Comparative Examples 1–3

In each of Examples 1–6 and Comparative Examples 1 and 2, a stock solution for an aerosol was prepared by combining the corresponding ingredients shown in Table 1. Using nitrogen gas (8 kg/cm$^2$) as a propellant, a pressurized one-pack aerosol was prepared. In each of Examples 7–9 and Comparative Example 3, on the other hand, a gel-like composition was prepared by combining the corresponding ingredients shown in Table 2. The resulting aerosols and gel-like compositions were ranked for their dyeing properties for goat hair and their severities of hair damage.

Each hair dye composition shown in Table 1 or 2 was applied at a weight ratio of 1:1 to goat hair and, after the hair was left over at 30° C. for 30 minutes, was rinsed off with water. The hair was dried and then ranked for dyeing properties and the severity of damage. The ranking was performed visually by 10 expert panelists in accordance with the below-described ranking 4-stage systems, and from the average scores obtained by the ranking, the dyeing properties and the severity of damage were determined in accordance with the below-described ranking standard. Incidentally, the developed color was red in each of Examples 3 and 9, and was black in each of the remaining Examples and the Comparative Examples.

(Ranking Systems)
  Dyeing properties (observation of dyed conditions with the naked eye):
   4: Very good
   3: Good
   2: A little poor
   1: Poor
  Severity of hair damage (comprehensive ranking based on observation of sleekness with the naked eye and touch):
   4: No damage in appearance and/or touch
   3: Only a little damage in appearance and/or touch
   2: Some damage in appearance and/or touch
   1: Damage in appearance and/or touch
(Ranking Standard)
   A: 3.5≦average score≦4
   B: 2.5≦average score<3.5
   C: 1.5≦average score<2.5
   D: 1≦average score<1.5

TABLE 1

| (wt. %) | Example | | | | | | Comp. Ex. | |
| --- | --- | --- | --- | --- | --- | --- | --- | --- |
|  | 1 | 2 | 3 | 4 | 5 | 6 | 1 | 2 |
| Toluene-2,5-diamine | 1.5 | 1.5 | 1.0 | 1.5 | 1.5 | 1.5 | 1.5 | 1.5 |
| p-Aminophenol | 0.5 | 0.5 | 0.3 | 0.5 | 0.5 | 0.5 | 0.5 | 0.5 |
| 2,4-Diaminophenoxyethanol | 0.2 | 0.2 | — | 0.2 | 0.2 | 0.2 | 0.2 | 0.2 |
| p-Amino-o-cresol | — | — | 0.7 | — | — | — | — | — |
| Sodium ascorbate | 0.1 | 0.1 | 0.1 | 0.1 | 0.1 | 0.1 | 0.1 | 0.1 |
| Disodium ethylenediaminetetraacetate | 0.3 | — | 0.3 | 0.3 | 0.3 | 0.3 | 0.3 | — |
| Trisodium ethylenediaminedisuccinate | — | 0.3 | — | — | — | — | — | — |
| Ferrous sulfate heptahydrate | 0.3 | 0.3 | 0.3 | 0.3 | 0.3 | 0.3 | — | 0.3 |
| Lauryl polyglucoside | 0.5 | 0.5 | 0.5 | 0.5 | — | 0.5 | 0.5 | 0.5 |
| Ethanol | 10 | 10 | 10 | 10 | 10 | 10 | 10 | 10 |
| 2-Benzyloxyethanol | — | — | — | 2 | — | — | — | — |
| Xanthan gum | 0.75 | 0.75 | 0.75 | 0.75 | 0.75 | 0.75 | 0.75 | 0.75 |

TABLE 1-continued

|  | Example | | | | | | Comp. Ex. | |
| --- | --- | --- | --- | --- | --- | --- | --- | --- |
| (wt. %) | 1 | 2 | 3 | 4 | 5 | 6 | 1 | 2 |
| 0.25 M Aqueous solution of sodium dihydrogenphosphate | 20 | 20 | 20 | 20 | 20 | 20 | 20 | 20 |
| Aqueous solution of sodium hydroxide | q.s.* | q.s.* | q.s.* | q.s* | q.s.* | q.s* | q.s.* | q.s.* |
| Water | Balance | Balance | Balance | Balance | Balance | Balance | Balance | Balance |
| pH | 7 | 7 | 7 | 7 | 7 | 9 | 7 | 7 |
| State of liquid upon application | Foamed | Foamed | Foamed | Foamed | Foamed a little | Foamed | Foamed | Foamed |
| Dyeing properties for goat hair (observed with naked eye) | A | A | A | A | B | B | D | D |
| Severity of damage | A | A | A | A | A | B | A | A |

*Amount sufficient to adjust the pH

TABLE 2

|  | Example | | |
| --- | --- | --- | --- |
| (wt. %) | 7 | 8 | 9 |
| Toluene-2,5-diamine | 1.5 | 1.5 | 1.0 |
| p-Aminophenol | 0.5 | 0.5 | 0.3 |
| 2,4-Diaminophenoxyethanol | 0.2 | 0.2 | — |
| p-Amino-o-cresol | — | — | 0.7 |
| Sodium ascorbate | 0.1 | 0.1 | 0.1 |
| Disodium ethylenediaminetetraacetate | 0.3 | — | 0.3 |
| Trisodium ethylenediaminedisuccinate | — | 0.3 | — |
| Ferrous sulfate heptahydrate | 0.3 | 0.3 | 0.3 |
| Lauryl polyglucoside | 0.5 | 0.5 | 0.5 |
| Ethanol | 10 | 10 | 10 |
| Polyquaternium-7 | 0.1 | 0.1 | 0.1 |
| Hydroxyethylcellulose | 1.00 | 1.00 | 1.00 |
| Sodium dihydrogenphosphate dihydrate | 0.78 | 0.78 | 0.78 |
| Aqueous solution of sodium hydroxide | q.s.* | q.s.* | q.s.* |
| Water | Balance | Balance | Balance |
| pH | 7 | 7 | 7 |
| State of liquid upon application | Foamed | Foamed | Foamed |
| Dyeing properties for goat hair (observed with naked eye) | A | A | A |
| Severity of damage | A | A | A |

The invention claimed is:

1. A hair dying process comprising:
applying to the hair an oxidizing-agent-free, air oxidative, one-pack hair dye composition, which consists essentially of an oxidation catalyst of two components ($a_1$) and ($a_2$) wherein
($a_1$) a water-soluble hydrochloride, sulfate, nitrate, carbonate, hydrogencarbonate, phosphate or organic acid salt of iron in an amount of 0.001 to 10 wt % in terms of the anhydrous form of the salt, based on the whole composition, and
($a_2$) a chelating agent selected from the group consisting of ethylenediaminetetraacetic acid, hydroxyethylethylenediaminetriacetic acid, ethylenediaminedisuccinic acid and salts thereof in an amount of 0.001 to 10 wt % based on the whole composition;
(b) a color-developing substance in an amount of 0.01 to 10 wt % based on the whole composition, to hair without mixing said hair dye composition with an oxidizing agent; and
(c) water; and
after allowing the hair to undergo treatment for 5 minutes to 1 hour, rinsing the applied hair dye composition from the hair with water.

2. A hair dying process comprising:
applying to the hair an oxidizing-agent-free, air oxidative, one-pack hair dye composition, which consists essentially of an oxidation catalyst of two components ($a_1$) and ($a_2$) wherein
($a_1$) a water-soluble hydrochloride, sulfate, nitrate, carbonate, hydrogencarbonate, phosphate or organic acid salt of iron in an amount of 0.001 to 10 wt % in terms of the anhydrous form of the salt based on the whole composition, and
($a_2$) a chelating agent selected from the group consisting of ethylenediaminetetraacetic acid, hydroxyethylethylenediaminetriacetic acid, ethylenediaminedisuccinic acid and salts thereof in an amount of 0.001 to 10 wt % based on the whole composition;
(b) a color-developing substance in an amount of 0.001 to 10 wt % based on the whole composition;
(d) a coupling substance;
(e) a surfactant, and (f) water without mixing said hair dye composition with an oxidizing agent; and
after allowing the hair to undergo treatment for 5 minutes to 1 hour, rinsing the applied hair dye composition from the hair with water.

3. The hair dyeing process according to claim 2, wherein the content of the surfactant (e) is present in the composition in an amount of 0.01 to 10 wt %, based on the whole composition.

4. The hair dyeing process according to claim 2, wherein the composition has a pH ranging from 6 to 8.

5. A hair dying process comprising:
applying to the hair an oxidizing-agent-free, air oxidative, one-pack hair dye composition, which consists essentially of an oxidation catalyst of two components ($a_1$) and ($a_2$) wherein
($a_1$) a water-soluble hydrochloride, sulfate, nitrate, carbonate, hydrogencarbonate, phosphate or organic acid salt of iron in an amount of 0.001 to 10 wt % in terms of the anhydrous form of the salt based on the whole composition, and
($a_2$) a chelating agent selected from the group consisting of ethylenediaminetetraacetic acid, hydroxyethylethylenediaminetriacetic acid, ethylenediaminedisuccinic acid and salts thereof in an amount of 0.001 to 10 wt % based on the whole composition;
(b) a color-developing substance in an amount of 0.001 to 10 wt % based on the whole composition;
(d) a coupling substance;
(e) a surfactant;
(f) a cationic polymer;

(g) a viscosity increasing agent, and (h) water without mixing said hair dye composition with an oxidizing agent; and after allowing the hair to undergo treatment for 5 minutes to 1 hour, rinsing the applied hair dye composition from the hair with water.

6. A hair dyeing process comprising: applying to the hair an oxidizing-agent-free, air oxidative, one-pack hair dye composition, which consists essentially of an oxidation catalyst of two components ($a_1$) and ($a_2$) wherein ($a_1$) a water-soluble hydrochloride, sulfate, nitrate, carbonate, hydrogencarbonate, phosphate or organic acid salt of iron in an amount of 0.001 to 10 wt% in terms of the anhydrous form of the salt based on the whole composition, and ($a_2$) a chelating agent selected from the group consisting of ethylenediaminetetraacetic acid, hydroxyethylethylenediaminetriacetic acid, ethylenediaminedisuccinic acid and salts thereof in an amount of 0.001 to 10 wt % based on the whole composition;

(b) a color-developing substance in an amount of 0.001 to 10 wt % based on the whole composition;

(d) a coupling substance;

(e) a surfactant;

(f) a cationic polymer;

(g) a viscosity increasing agent;

(h) an organic solvent, to hair without mixing said hair dye composition with an oxidizing agent; and after allowing the hair to undergo treatment for 5 minutes to 1 hour, rinsing the applied hair dye composition from the hair with water.

7. A hair dyeing process comprising:

applying to the hair an oxidizing-agent-free, air oxidative, one-pack hair dye composition, which consists essentially of an oxidation catalyst of two components ($a_1$) and ($a_2$) wherein ($a_1$) a water-soluble hydrochloride, sulfate, nitrate, carbonate, hydrogencarbonate, phosphate or organic acid salt of iron in an amount of 0.001 to 10 wt % in terms of the anhydrous form of the salt based on the whole composition, and ($a_2$) a chelating agent selected from the group consisting of ethylenediaminetetraacetic acid, hydroxyethylethylenediaminetriacetic acid, ethylenediaminedisuccinic acid, and salts thereof in an amount of 0.001 to 10 wt % based on the whole composition;

(b) a color-developing substance in an amount of 0.001 to 10 wt % based on the whole composition;

(d) a coupling substance;

(e) a surfactant;

(f) a cationic polymer;

(g) a viscosity increasing agent;

(h) an organic solvent;

(i) at least one additive selected from the group consisting of higher alcohols, stabilizers, buffering agents, fragrances, touch improvers, solubilizers, polyols, direct dyes, oxidative dyes, basic dyes, disperse dyes, oxidation inhibitors and preservatives, (j) water; and without mixing said hair dye composition with an oxidizing agent; and after allowing the hair to undergo treatment for 5 minutes to 1 hour, rising the applied hair dye composition from the hair with water.

8. The hair dyeing process according to claim 6, wherein said surfactant is represented in a proportion ranging from 0.01 to 10 wt % based on the whole composition.

9. The hair dyeing process according to claim 7, wherein said surfactant is represented in a proportion ranging from 0.01 to 10 wt % based on the whole composition.

10. The hair dyeing process according to claim 1, wherein said iron salt is ferrous sulfate or ferrous chloride.

* * * * *